(12) United States Patent
Schwarz et al.

(10) Patent No.: US 10,039,929 B1
(45) Date of Patent: Aug. 7, 2018

(54) METHOD AND DEVICE FOR PELVIC FLOOR TISSUE TREATMENT

(71) Applicant: BTL HOLDINGS LIMITED, Nicosia (CY)

(72) Inventors: Tomáš Schwarz, Prague (CZ); Lucia Kosturiakova, Varin (SK); Jan Milichovsky, Cernovice (CZ)

(73) Assignee: BLT Holdings Limited, Nicosia (CY)

( * ) Notice: Subject to any disclaimer, the term of this patent is extended or adjusted under 35 U.S.C. 154(b) by 0 days.

(21) Appl. No.: 15/478,943

(22) Filed: Apr. 4, 2017

(51) Int. Cl.
*A61N 7/02* (2006.01)
*A61H 23/00* (2006.01)
*A61N 2/00* (2006.01)
*A61N 1/40* (2006.01)
*A61N 5/06* (2006.01)
*A61N 1/36* (2006.01)
*A61N 7/00* (2006.01)

(52) U.S. Cl.
CPC ......... *A61N 2/002* (2013.01); *A61N 1/36007* (2013.01); *A61N 1/40* (2013.01); *A61N 2/004* (2013.01); *A61N 5/0603* (2013.01); *A61N 7/00* (2013.01); *A61N 2005/0611* (2013.01); *A61N 2007/0043* (2013.01)

(58) Field of Classification Search
CPC .. A61N 2007/0034; A61N 1/08; A61N 2/006; A61N 2/02; A61N 5/0603; A61N 2/002; A61N 2/008
See application file for complete search history.

(56) References Cited

U.S. PATENT DOCUMENTS

| | | |
|---|---|---|
| 3,915,151 A | 10/1975 | Kraus |
| 4,665,898 A | 5/1987 | Costa |
| 4,993,413 A | 2/1991 | McLeod |
| 5,085,626 A | 2/1992 | Frey |
| 5,249,585 A * | 10/1993 | Turner ............ A61B 5/01 600/549 |
| 5,401,233 A | 3/1995 | Erickson et al. |
| 5,766,124 A | 6/1998 | Polson |

(Continued)

FOREIGN PATENT DOCUMENTS

EP 0209246 A1 1/1987
EP 2676700 A2 12/2013

(Continued)

OTHER PUBLICATIONS

Lin, et al., "Functional Magnetic Stimulation: A New Modality for Enhancing Systemic Fibrinolysis," Arch Phys Med Rehabil vol. 80, May 1999, pp. 545-550.

(Continued)

*Primary Examiner* — Christine H Matthews
*Assistant Examiner* — Joshua D Lannu
(74) *Attorney, Agent, or Firm* — Kenneth H. Ohriner; Perkins Coie LLP

(57) ABSTRACT

Methods and devices for pelvic floor tissue treatment involve positioning at least one applicator adjacent to the pelvic floor tissue and transferring energy into the tissue, causing a biological effect in the tissue. The applicator may have a detachable part which can be changed to better provide specific treatments. The detachable part may contain at least one energy delivery element providing one type of energy for use in providing the treatment.

30 Claims, 6 Drawing Sheets

(56) References Cited

U.S. PATENT DOCUMENTS

| | | | |
|---|---|---|---|
| 5,769,778 A * | 6/1998 | Abrams | A61N 1/08 |
| | | | 128/897 |
| 5,984,854 A * | 11/1999 | Ishikawa | A61N 2/02 |
| | | | 600/9 |
| 6,179,769 B1 | 1/2001 | Ishikawa et al. | |
| 6,213,933 B1 | 4/2001 | Lin | |
| 6,223,750 B1 | 5/2001 | Ishikawa et al. | |
| 6,402,678 B1 | 6/2002 | Fischell et al. | |
| 6,418,345 B1 | 7/2002 | Tepper | |
| 6,527,694 B1 | 3/2003 | Ishikawa et al. | |
| 6,569,078 B2 | 5/2003 | Ishikawa et al. | |
| 6,939,287 B1 | 9/2005 | Ardizzone et al. | |
| 7,030,764 B2 | 4/2006 | Smith et al. | |
| 7,601,115 B2 | 10/2009 | Riehl | |
| 7,740,574 B2 | 6/2010 | Pilla et al. | |
| 7,744,523 B2 | 6/2010 | Epstein | |
| 7,946,973 B2 | 5/2011 | Peterchev | |
| 7,998,053 B2 | 8/2011 | Aho | |
| 8,088,058 B2 | 1/2012 | Juliana et al. | |
| 9,002,477 B2 | 4/2015 | Burnett | |
| 2001/0031906 A1 | 10/2001 | Ishikawa et al. | |
| 2003/0139788 A1 * | 7/2003 | Eggers | A61B 18/04 |
| | | | 607/96 |
| 2006/0152301 A1 | 7/2006 | Rohwedder | |
| 2006/0187607 A1 | 8/2006 | Mo | |
| 2008/0262287 A1 | 10/2008 | Dussau | |
| 2008/0306325 A1 * | 12/2008 | Burnett | A61N 2/02 |
| | | | 600/13 |
| 2009/0005631 A1 | 1/2009 | Simenhaus | |
| 2010/0087699 A1 | 4/2010 | Peterchev | |
| 2010/0179372 A1 | 7/2010 | Glassman | |
| 2010/0331603 A1 | 12/2010 | Szecsi | |
| 2011/0021863 A1 | 1/2011 | Burnett | |
| 2011/0263925 A1 | 10/2011 | Bratton | |
| 2012/0053449 A1 | 3/2012 | Moses | |
| 2012/0065494 A1 * | 3/2012 | Gertner | A61B 5/055 |
| | | | 600/411 |
| 2013/0030239 A1 | 1/2013 | Weyh | |
| 2013/0123568 A1 | 5/2013 | Hamilton | |
| 2013/0158634 A1 | 6/2013 | Edoute | |
| 2013/0238061 A1 | 9/2013 | Edoute | |
| 2013/0317281 A1 | 11/2013 | Schneider | |
| 2014/0046423 A1 | 2/2014 | Rajguru | |
| 2015/0025299 A1 | 1/2015 | Edoute | |
| 2015/0123661 A1 | 5/2015 | Yui | |
| 2015/0133717 A1 | 5/2015 | Ghiron | |
| 2015/0157873 A1 | 6/2015 | Sokolowski | |
| 2015/0328475 A1 | 11/2015 | Kim | |
| 2015/0367141 A1 | 12/2015 | Goetz | |
| 2016/0051827 A1 | 2/2016 | Edoute | |
| 2016/0220302 A1 * | 8/2016 | Zarins | A61F 6/20 |

FOREIGN PATENT DOCUMENTS

| | | | |
|---|---|---|---|
| WO | 2002025675 A1 | 3/2002 | |
| WO | 2003090863 A1 | 11/2003 | |

OTHER PUBLICATIONS

U.S. Patent and Trademark Office, Non-final Office Action issued in U.S. Appl. No. 15/344,811 dated Mar. 28, 2017.

* cited by examiner

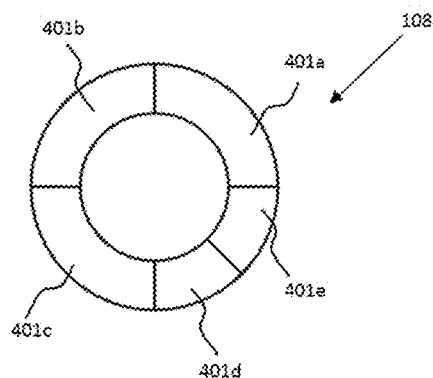
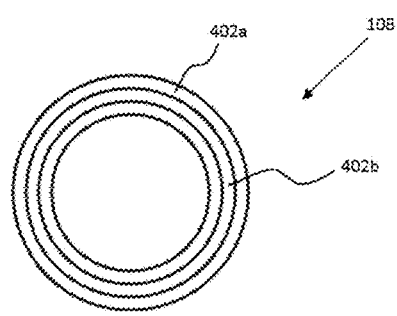
FIG 4A          FIG 4B
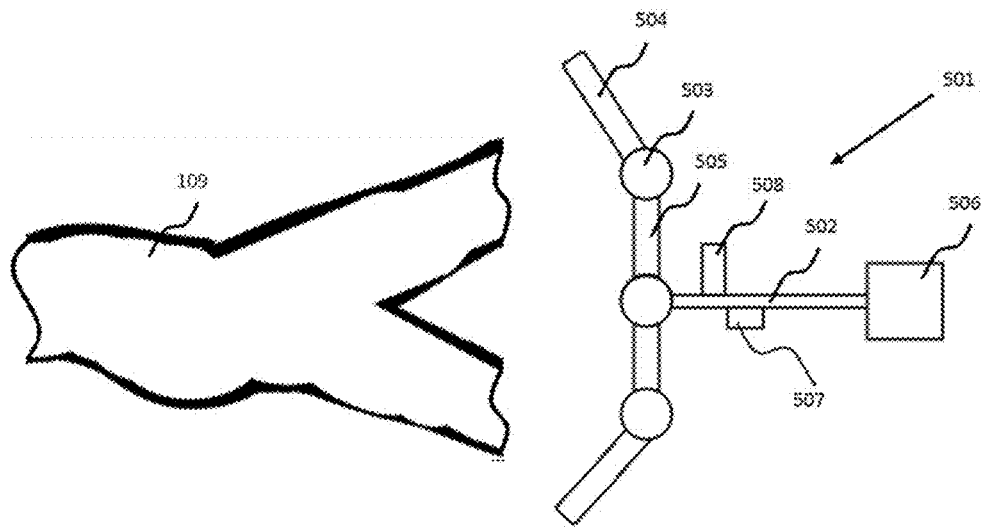
FIG 5A

METHOD AND DEVICE FOR PELVIC FLOOR TISSUE TREATMENT

FIELD OF THE INVENTION

This invention relates to apparatus and methods for genital rejuvenation, remodelling, treatment of sexual dysfunction, gynaecological treatment and treatment of organs or tissues located in or near the pelvic floor.

BACKGROUND

The pelvic floor is formed in a bowl-like structure and contains tissues and organs including the male or female genitals, urethra, bladder or rectum. Pelvic floor organs and tissue include cavities. Dysfunction of the pelvic floor may be demonstrated, for example, by incontinence, rectal/anal canal prolapse, vaginal prolapse, chronic pain, functional constipation, infections and inflammations. It may be also demonstrated by sexual problems like erectile, ejaculatory and orgasmic dysfunction or dyspareunia. The muscle contraction may be responsible for some functions of the pelvic floor, while the connective tissue (including collagen, elastin, fibronectin, laminins, glycoproteins, proteoglycans and/or matricellular proteins) provides structural support for the pelvic floor organs.

The female genital tissue contains the vulva and vagina. The vulva is an external, visible part of the female genital tissue including the mons pubis, labia majora, labia minora, hymen, clitoris, vaginal opening and urethral orifice. Perineum is a tissue part located below genital tissue. The labia minora and vaginal opening forms cavity called vulvar vestibule. While the mons pubis, labia majora and perineum have a fully keratinized, stratified squamous epithelium, the degree of keratinization of the labia minora declines from the outer surface to the inner surface. The mons pubis and labia majora include fatty tissue and loose connective tissue. The labia minora has mainly connective tissue and some smooth muscle fibres making it an erectile structure. The clitoris contains erectile tissue and connective tissue. The human vagina is a canal composed of four layers, the outermost is the epithelium, below which extends a subepithelial layer called the lamina propria, the muscularis and in the innermost is the adventitia.

There are few therapeutic approaches to treat female genital tissue. For example, in case of vaginal prolapse or rejuvenation, surgery of the pelvic floor or unnecessary tissue may be performed. Such method is painful and requires invasive treatment of sensitive areas. Another approach, used for vaginal and vulvar rejuvenation, utilizes the electromagnetic energy for denaturation of existing tissue to induce the deposition of a newly synthetized tissue. However, this method requires the operator to move the applicator over treated area, which may cause discomfort for the patient. The shape of already used applicator is also a limitation of such methods.

This method includes delivering only one type of energy and requires uncomfortably long and repeated treatment sessions. It may also not provide sufficient treatment without the risk of relapse.

Another limitation of known treatments is the inappropriate shape of applicators for delivering the energy. Such applicators deliver energy only to the part of the tissue. Therefore the biological effect is induced only in the affected portion of the tissue. Treatment may require repeated repositioning and continuous movement of the applicator in order to treat the intended tissue part. Moreover, the shape and technical solution of such applicators does not allow their adaptability to the patient. The medical professional and patient may therefore face problems during the treatment related to the rigid and fixed construction of the applicator and the shape of the treated pelvic floor tissue. Such problems may lead to ineffective, uncomfortable and even painful treatment.

Also, the existing therapeutic approaches for the treatment of other parts of the pelvic floor, for example the rectum, anus and the perineum, use invasive surgical methods or have similar disadvantages as described above. In particular, the treatment of fecal incontinence is mainly targeted to the muscle structure of the sphincters. Presently, this approach uses invasive electrodes to stimulate the muscle and therefore it may be painful for the patient. The treated tissue may become more sensitive and it may lead to problems after treatment.

Furthermore, the currently used methods for treating pelvic floor tissues and organs are contact or even invasive methods and may cause discomfort to the patient by the necessity of uncovering an intimate part of the body. Another disadvantage is discomfort caused by the touching of the intimate parts of the body by medical professional. As a result, patients may avoid treatment of the pelvic floor tissue, which may lead to worsening of their condition.

There is a need for new methods and devices for treatment of pelvic floor tissues and organs.

SUMMARY OF THE INVENTION

The present methods and devices may be used for treatment of tissue by application of energy.

Devices and methods apply combination of at least two different types of energy. Such combination of types of energy may provide faster and more consistent treatment of the tissue with the long lasting results.

A first type of energy may be replaced by second type of energy. Alternatively the first and second type of energies may be supplied simultaneously by one or more applicators. The energy may be any kind of electromagnetic energy (e.g. light, radiofrequency energy and/or microwave energy); mechanical energy (e.g. acoustic wave, ultrasound wave or shock wave), electric, magnetic energy and/or plasma. Treatment may require different energy types, depth, power and/or focus.

The applicator may have one or more detachable parts. A detachable part may include one or more energy delivery elements or no energy delivery elements.

Alternatively, the detachable part may include at least two energy delivery elements delivering different types of energy. Detachable parts may be combined and/or assembled to create an applicator of any size, shape, length, width, type of energy and/or elasticity. Therefore, the user may change the applicator by attaching at least one detachable part to the applicator.

The method and device may be used for treatment of many health issues of the pelvic floor tissue for e.g. maintaining of stability of vaginal environment, vaginal laxity or treating of issues associated with anal and rectum. Furthermore, the method and device may be also used for treatment of erectile issues related to the penis, mons pubis and other tissues.

Internal and external applicators may be used separately or together. The applicator may be implemented in garments and/or may be worn on the body during normal activities. A system may include expandable elements ensuring the delivery of the energy adjacent to the tissue.

Energy may be delivered to the patient in a self-operated manner i.e. operated without the continuous supervision and/or manual action of an operator. This saves time and cost, because the operator may simultaneously treat more than one patient. A self-operated device containing a self-operated applicator may minimize and/or prevent mistakes of a human operator, e.g. burning of the tissue. The device may be also incorporated into a supporting structure, e.g. a chair or bed.

Optionally, the device and method may include application of the energy by the applicator with direct contact, indirect contact or no contact with the tissue. In case of no contact, the applicator may be spaced apart from the tissue by a gap. This configuration may be used for treatment without need of undressing and touching the patient.

GLOSSARY

The term "energy" means any type of energy or field applied by the device. It may be electromagnetic energy which may be light, radiofrequency energy and/or microwave energy, mechanical energy which may be ultrasound energy and/or shock wave energy, magnetic energy, electric energy, thermal energy and/or plasma. The energy may be unfocused and/or focused to one or more one areas. The energy may include coherent and/or non-coherent energy.

The term "direct contact" means any contact of the applicator of the device with the tissue.

The term "indirect contact" means any contact of the applicator with the tissue through spacing object.

The term "no contact" means the applicator is spaced apart from the tissue by a gap.

The term "biological effect" means any one or more of: a cell death, apoptosis, necrosis, analgesic effect, blood flow enhancement, change of pH, partial denaturation of tissue and/or any part of the tissue, contraction of the tissue, muscle contraction, relaxation of the tissue, dilatation of the tissue, rejuvenation of the tissue, pain relief, restoration of the connective tissue, altering the shape and/or volume of the tissue, influence on protein synthesis, influence on activity of at least one enzyme, influence on cell metabolism, neocollagenesis, neoelastinogenesis and/or synthesis of any other part of connective tissue, stimulation of hormones, resurfacing of the tissue and/or any other result of applied energy on biological tissue. Disclosed types of biological effect may be combined.

The term "tissue" means in particular but not exclusively pelvic floor tissue including genital tissue, internal tissue of and/or external tissue surrounding the vagina, uterus, vulva, labia minora, labia majora, lamina propria, adjacent muscles, clitoris, cervix, perineum, penis, scrotum, anal canal, rectum. In addition the term "tissue" means mouth, earlobes and/or nose. It may also mean any layer and/or volume of tissue, such as epithelial surface, dermis, adipose tissue, muscularis, mucosal tissue, submucosal layer and gingiva.

The term "treated tissue" means at least part of the surface and/or volume of the tissue influenced by the treatment.

The term "energy delivery element" means an element providing energy to the patient. Also, the term "energy delivery element" should be understood as an energy providing element with additional parts; for example, the ultrasound transducer together with the backing material, coupling liquid and acoustic window.

BRIEF DESCRIPTION OF THE DRAWINGS

FIG. 4A is an exemplary view of the energy delivery element

FIG. 4B is another exemplary view of the energy delivery element

FIG. 5A is a view of an exemplary external applicator.

DETAILED DESCRIPTION OF THE INVENTION

Figure 1A:
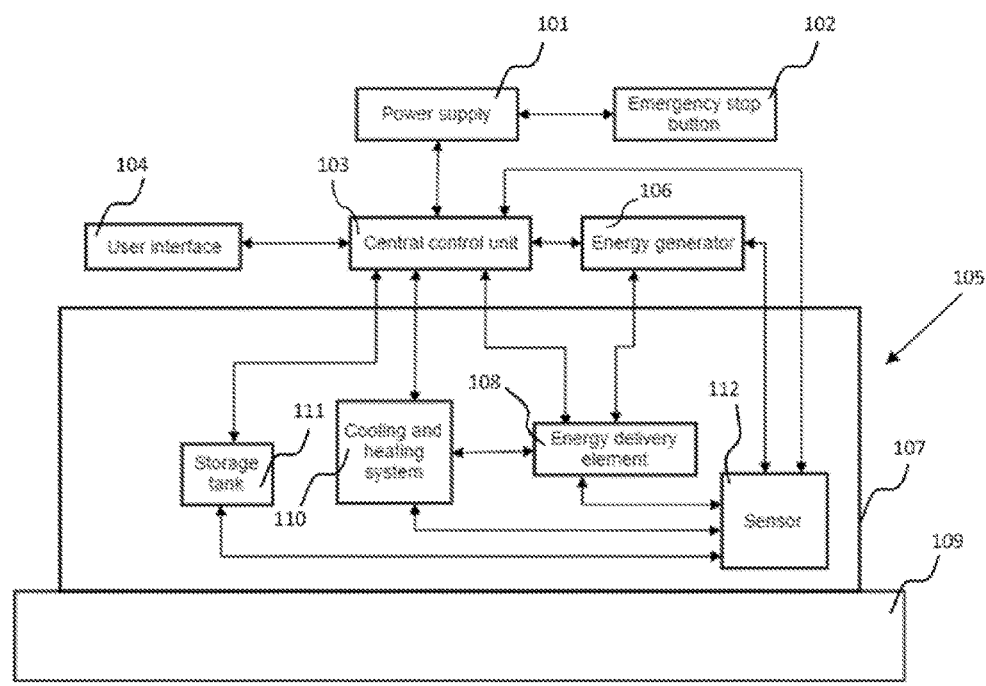
FIG. 1A is schematic diagram of a device for treatment of tissue.

Genital tissue may be divided to female genital tissue and male genital tissue. The external male genital tissue contains the penis and scrotum, internal male genital tissue contains the epididymis, vas deferens and accessory glands. The penis includes erectile tissue. The female genital tissue contains the vulva and vagina. The vulva is an external visible part of the female genital tissue including the mons pubis, labia majora, labia minora, hymen, clitoris, vulvar vestibule, vaginal opening and urethral orifice. Parts of the vulva contain the epithelium, connective tissue and muscularis. The labia majora and mons pubis also contain adipose tissue. The vulva is separated from the anal canal by the perineum.

The human vagina is a canal composed of four layers. The outermost is the epithelium including a nonkeratinized squamous layer. The vaginal epithelium is formed of stratified cells containing a high content of glycogen.

The epithelium may also include bacteria. After desquamation of the stratified cells, the glycogen may be released from the cells and metabolized by lactic bacteria to lactic acid, reducing the pH of the vaginal environment to pH between 4 and 5. Low pH may protect the vagina from colonization by other possibly dangerous bacteria and therefore protect vagina from the inflammation. Some species of bacteria, for example *Lactobacillus, Leptotrichia* and/or *Megashera*, may further improve vaginal health by producing and releasing bacteriocins and other antimicrobial compounds. Colonization of vaginal epithelium by particular bacteria species may be associated with reduced tendency of acquisition and/or transmission of sexually transmitted pathogens. In addition, the presence of particular bacteria may be associated with lower risk of pregnancy-related complications, including pre-term labor. In general, the state of vaginal tissue may help to maintain stability of vaginal environment and health.

A second subepithelial layer, called lamina propria, is a dense tissue layer including fibrillary proteins, collagen, elastin, blood vessels and/or lymphatic vessels. Transudate from these vessels, together with cervical mucus, provides lubrication before and/or during sexual intercourse. Lamina propria includes fibroblasts synthetizing the fibrilllar proteins, e.g. collagen and/or elastin. In addition, the fibrillary proteins may be synthetized by smooth muscle cells. Collagen provides vaginal tissue firmness, while the elastin provides extensibility and elastic recoil. The collagen molecules are formed by a triple-helix fibre structure. Elastin forms an elastic matrix and elastic fibres. Elastin biosynthesis is unique among connective tissue proteins by its limitation to a brief period of development, when elastic fibres produced in the third trimester of foetal life last the rest of life. This limitation, related to most organs and undisturbed tissues, is not present in the female genital tissue, where elastic fibre turnover is continuous.

The third layer, the muscularis, includes smooth muscles. Muscularis and lamina propria, provide a tensile firmness to the vaginal wall. Muscles are in complex interaction with connective tissue of the urethra and vaginal wall.

The fourth layer, the adventitia, is a connective tissue layer separating the muscularis of the vagina and paravaginal tissue. The adventitia contains elastin, collagen and fibroblasts, which may synthetize them. The adventitial fibroblasts may produce fibronectin. Fibronectin is essential for the conversion of fibroblasts to activated myofibroblasts involved in complex cellular functions including tissue repair.

Connective tissue contains at least one protein e.g. collagen; elastin; fibronectin; laminins; glycoproteins; proteoglycans and/or matricellular proteins.

Collagen includes twenty-eight different collagen types which are synthesized by cells, mainly by fibroblasts and/or by muscles. Fibrillar collagen (types I, II, III, V, XI. XXIV and XXVII) provide strength, while other types may interact with basal membrane and/or with the fibrillary collagen in order to link the fibrils together or with other molecules of extracellular matrix. Elastin is a stable protein and provides elasticity.

Proteoglycans and glycoproteins interact with growth factors, cytokines and chemokines, cell surface receptors and other molecules of extracellular matrix. They participate in cell procedures such as signalling, proliferation, migration, differentiation, apoptosis and adhesion.

Fibronectin is another fibrillar protein synthesized primarily by fibroblasts. Laminins are glycoproteins influencing cell migration, adhesion and differentiation. They also contribute to blood vessel growth and maturation.

Matricellular proteins play role in organization of extracellular matrix, namely in collagen fibrils, elastin and fibronectin arrangement. They also have significant role in the interactions of the molecules of the extracellular matrix.

Methods and devices are described for prevention and/or treatment of vaginal laxity, vulvar laxity, vaginal dryness by improving humidity, stabilization of vaginal environment, vulvar atrophy, vaginal atrophy, stress urinary incontinence, dysmenorrhea, dyspareunia, muscle spasms, anorectal abscess, anal fistula, rectal pain, haemorrhoids and or anal laxity. These methods and devices may also be used for sexual enhancement, erectile issues, increase of local circulation (e.g. blood or lymph). Other treatments may include prevention and/or treatment of cervicitis, vaginitis, abscess of vulva, bartholinitis, cervical dysplasia, vulvar dysplasia, vaginal dysplasia, leukoplakia of cervix, leukoplakia of vagina, tight vaginal opening, genital warts, candiasis, lichen planus, vulval dermatitis, prostatic hyperplasia and/or vulvar hypertrophy, vaginal bleaching and anal bleaching. The present methods and devices may also be used for labia majora alteration, labia minora alteration and/or clitoral hood reduction.

Treatment of vaginal, vulvar and anal laxity by tightening the tissue may provide increased sexual pleasure. Treatment of erectile tissue located in mons venus, penis, vulvar vestibule, labia minora and/or clitoris may induce angiogenesis, repair of the tissue, synthesis of the tissue and/or enhancement of local circulation.

The present methods and devices may induce a biological effect. The energy transfer may cause at least partial denaturation of connective tissue (e.g. collagen, elastin, fibronectin). It may lead to rejuvenation and/or deposition of at least part of connective tissue by fibroblasts and/or smooth muscle cells or lead to proliferation of at least one fibroblast to myofibroblast.

The method may include application of energy to at least one tissue layer and/or a volume of the tissue, such as the pelvic floor, genital tissue, tissues of perineal region and/or canals. Treatment may be contact, indirect contact and/or with no contact provided by the device positioned adjacent to the tissue of the patient. Energy may be applied in a continuous and/or pulsed manner.

The energy transfer may be used for improvement of activity of at least one enzyme e.g. at least one of lysyl oxidase, matrix metalloproteases and/or drug-metabolizing enzymes. Vaginal environment stability may be maintained by application of energy to the tissue to enhance proliferation and/or desquamation of at least one layer. Desquamated tissue containing glycogen may be utilized as a nutrient supply by bacteria, including *Lactobacillus* species, *Leptotrichia* and/or *Megashera*.

The application of electromagnetic energy may lead to heating of the tissue. Energy flux provided by radiofrequency energy may be in the range of 0.001 W·cm$^{-2}$ to 1500 W·cm$^{-2}$, more preferably in the range of 0.01 W·cm$^{-2}$ to 1000 W·cm$^{-2}$, most preferably in the range of 0.5 W·cm$^{-2}$ to 500 W·cm$^{-2}$.

The heating may induce the relaxation of the heated tissue, blood flow enhancement, relief of pain and/or at least partial denaturation of the connective tissue and/or its parts. Heating may also induce analgesic effects and/or myorelaxation.

In one embodiment the radiofrequency energy may be in the range of 10 kHz to 300 GHz, more preferably in the range of 300 kHz to 10 GHz, most preferably in the range of 400 kHz to 6 GHz. In another embodiment, the radiofrequency energy may be in the range of 100 kHz to 550 MHz, more preferably in the range of 250 kHz to 500 MHz, even more preferably in the range of 350 kHz to 100 MHz, most preferably in the range of 500 kHz to 80 MHz. Output may be up to 450, 300, 250 or 200 W. The method and device may include operation of the device in the ISM bands of 6.78 MHz, 13.56 MHz, 27.12 MHz, 40.68 MHz, 433.92 MHz, 915 MHz, 2.45 GHz and 5.8 GHz.

Applied energy may include light which may provide heating, myorelaxation effect and/or biostimulation. Light in the range of 620 to 750 nm may be beneficial for local circulation enhancement, restoration of connective tissue, light in the range of 400 to 500 nm may provide bactericidal effect, light in the range of 560 to 60 nm may stimulate tissue rejuvenation. All these types of light may be applied.

Light may be monochromatic or polychromatic. Light may be applied in pulses with duration in the range of 0.1 μs to 10000 ms, more preferably in the range of 1 μs to 5000 ms, even more preferably in the range of 2 μs to 2500 ms, most preferably in the range of 5 μs to 1000 ms. The wavelength of the light may be in the range of 200 nm to 15000 nm, more preferably in the range of 250 nm to 10000 nm, even more preferably in the range of 300 nm to 5000 nm, most preferably in the range of 400 nm to 3000 nm. Energy flux provided by light may be in the range of 0.005 W·cm$^{-2}$ to 75 W·cm$^{-2}$, more preferably in the range of 0.01 W·cm$^{-2}$ to 60 W·cm$^{-2}$ and most preferably in the range of 0.01 W·cm$^{-2}$ to 50 W·cm$^{-2}$. Method and device may also include spot size defined as surface of tissue treated by the light. Spot size may be in the range of 0.01 cm$^2$ to 600 cm$^2$, more preferably in the range of 0.05 cm$^2$ to 550 cm$^2$, most preferably in the range of 0.1 cm$^2$ to 520 cm$^2$.

Energy may be also applied in the narrower spectral band. Some of the spectral bands may represent different colors of the visible part of the electromagnetic spectrum. The wavelength of the applied light may be close to 254 nm, 405 nm, 450 nm, 530 nm, 560 nm, 575 nm, 640 nm, 685 nm, 830 nm and/or 1064 nm. Term "close to" refers to deviation of 20%, more preferably 15%, most preferably 10% from the nominal wavelength.

According to one embodiment, the low level light may be used. The output of the source may be in the range of 0.1 mW to 600 mW, more preferably in the range of 1 mW to 500 mW, even more preferably in the range of 1.5 mW to 475 mW, most preferably in the range of 3 mW to 450 mW. Energy flux provided by low level light may be in the range of 0.01 W·cm$^{-2}$ to 30 W·cm$^{-2}$, more preferably in the range of 0.05 W·cm$^{-2}$ 25 W·cm$^{-2}$ and most preferably in the range of 0.1 W·cm$^{-2}$ 20 W·cm$^{-2}$.

According to another embodiment, high level light may be used. In this case, the output of the source may be in the range of 0.1 W to 30 W, more preferably in the range of 0.2 W to 25 W, most preferably in the range of 0.35 W to 15 W. Energy flux provided by high level light may be in the range of 0.01 W·cm$^{-2}$ to 50 W·cm$^{-2}$, more preferably in the range of 0.05 W·cm$^{-2}$ to 40 W·cm$^{-2}$ and most preferably in the range of 0.1 W·cm$^{-2}$ to 35 W·cm$^{-2}$.

Applied energy may include mechanical energy. Mechanical energy may provide focused and/or unfocused heating, cavitation, microbubbles formation, muscle stimulation, stimulation of healing process, blood flow stimulation and/or stimulation of inflammatory response.

Optionally, the application of the mechanical energy may lead to creation of focus in desired depth of the tissue and/or defocusing the energy into larger area of the tissue. Treatment depth of the mechanical energy may be in the range of 0.1 to 100 mm, more preferably in range of 0.2 mm to 50 mm, most preferably in range of 0.25 mm to 25 mm, most preferably in range of 0.3 to 15 mm under the surface of treated tissue. Treatment depth may be influenced by focusation, defocusation and/or frequency of mechanical energy.

The frequency of the ultrasound energy may be in the range of 20 kHz to 25 GHz, more preferably in the range of 20 kHz to 1 GHz, even more preferably in the range from 50 kHz to 250 MHz, most preferably in the range of 100 kHz to 100 MHz. Energy flux provided ultrasound energy may be in the range of 0.001 W·cm$^{-2}$ to 500 W·cm$^{-2}$, more preferably in the range of 0.005 W·cm$^{-2}$ to 350 W·cm$^{-2}$, most preferably in the range of 0.05 W·cm$^{-2}$ to 250 W·cm$^{-2}$.

Mechanical energy may be shock wave energy, where shock waves may provide pain relief, blood flow enhancement, myorelaxation and mechanical stimulation.

Shock waves are characterized by steep pressure amplitude growth in comparison to the surrounding pressure and their non-linear wave propagation. Also, shock waves are characterized by swift positive pressure increase with positive peak pressure amplitudes in the range of 0.1 MPa to 150 MPa or 3 MPa to 150 MPa or 7 MPa to 150 MPa. Shock wave energy may be generated by electrohydraulic, piezoelectric, electromagnetic, pneumatic and/or ballistic principle. The repetition rate of shock wave energy may be in the range of 0.1 Hz to 1000 Hz, more preferably in the range of 0.1 Hz to 750 Hz, even more preferably in the range of 0.5 Hz to 600 Hz most preferably in the range of 1 Hz to 500 Hz.

Energy flux provided by shock wave energy may be in the range between 0.0001 W·cm$^{-2}$ and 50 W·cm$^{-2}$, more preferably in the range between 0.0001 W·cm$^{-2}$ and 35 W·cm$^{-2}$, most preferably in the range between 0.0001 W·cm$^{-2}$ and 25 W·cm$^{-2}$.

In one embodiment ballistic shock waves may be used. Ballistic shock waves may be generated by striking of a bullet inside a guiding tube to a percussion guide. The bullet may be accelerated by pressurized gas, spring, electric field, magnetic field or other technique. The repetition rate of the ballistic shock wave may be in the range of 0.1 Hz to 150 Hz or 0.5 Hz to 100 Hz or 1 Hz to 60 Hz.

Applied energy may be electric energy which may provide muscle stimulation, analgesic effect, contraction of muscles and/or myorelaxation effect.

Electric energy may be applied in a constant current mode. In this case the, output current may be in the range of 0.01 mA to 400 mA or 0.01 mA to 300 mA, or 0.01 mA to 180 mA. Output voltage may be in the range of 0.001 V to 350 V or 0.001 V to 300 V or 0.001 V to 250 V.

Electric energy may be applied in a constant voltage mode. In this case, the output current may be in the range of 0.01 mA to 400 mA or 0.01 mA to 00 mA or 0.01 mA to 180 mA. Output voltage may be in the range of 0.001 V to 350 V or 0.001 V to 300 V or 0.001 V to 250 V.

Electric energy may provide the high voltage therapy. In this case, the output current may be in the range of 0.01 mA to 50 mA or 0.01 mA to 30 mA or 0.01 mA to 15 mA. Output voltage may be in the range of 0.001 V to 800 V or 0.001 V to 650 V or 0.001 V to 600 V.

In a microcurrent application, the output current may be in the range of 0.001 mA to 10 mA or 0.001 mA to 5 mA or 0.001 mA to 3 mA. Output voltage may be in the range of 0.001 V to 250 V or 0.001 V to 200 V or 0.001 V to 150 V.

Electric energy may be applied in pulses. The repetition rate of pulses may be in the range of 0.001 Hz to 1000 Hz or 0.05 Hz to 800 Hz or 0.1 to 600 Hz. The repetition rate of pulses may induce various effects. The repetition rate of pulses inducing muscle stimulation may be in the range of 0.01 Hz up to 100 Hz or 0.05 Hz to 85 Hz or 0.1 Hz to 75 Hz. The repetition rate of pulses inducing pain relief may be in the range of 100 Hz up to 400 Hz or 105 Hz to 250 Hz or 115 Hz to 150 Hz. The repetition rate of pulses inducing a myorelaxation may be in the range of 100 Hz up to 600 Hz or 130 Hz to 400 Hz or 150 Hz to 250 Hz. Amplitude of applied current may vary following the patient needs and/or desired effect.

Applied energy may be magnetic energy which may provide at least partial muscle contraction, myorelaxation effect, stimulation of one or more muscle fibre and/or analgesic effect. A device and method for generation of magnetic energy is described in co-pending applications PCT/IB2016/053930, U.S. 62/357,679, U.S. Ser. No. 15/396,073, U.S. Ser. No. 15/404,384, U.S. Ser. No. 15/344,811, U.S. Ser. No. 15/073,318 which are incorporated herein by reference. Magnetic flux density of the magnetic energy may be at least 0.1, 0.5, 1, 2 T or up to 7 T at repetition rate at least 0.1, 1, 10, 30, 50, 55, 60 or up to 700 Hz with treatment/successive treatments lasting several seconds or longer, for example, for at least 5, 10, 30, 60, 120 or 240 seconds or longer. The impulse duration may be in the range of tens to hundreds of μs. The magnetic energy may by static and/or time variable (e.g. monophasic or biphasic)

The magnetic energy may be modulated. In one embodiment the magnetic flux density is varied, while the repetition rate of the time varying magnetic energy is the same as impulse duration. In another embodiment the repetition rate may be varied while the impulse duration and magnetic flux density is constant. In still another embodiment the impulse duration may be varied while the repetition rate and magnetic flux density may remain constant.

Applied energy may be plasma such as nonthermal plasma (called also cold plasma) may be used. Application of plasma may be used for reduction and/or elimination the possible discomfort of the patient (e.g. bleeding, pain) before, during and/or after the treatment. Application of nonthermal plasma may stimulate regenerative processes by wound healing enhancement and or blood coagulation. Nonthermal plasma may be bactericide and therefore may decrease the risk of the inflammation.

Plasma may be also supplemented by another substance e.g. gas, radical, radical precursor and/or radical scavenger. The other substance may be nitric oxide and its radicals. Temperature of generated plasma may be between 18° C. to 65° C., more preferably between 25° C. to 62° C., even more preferably between 30° C. to 60° C., most preferably between 32° C. to 40° C. Plasma may be applied in range between 1 s to 60 min, preferably between 10 s to 40 min, even more preferably between 30 s to 30 min. Plasma may also be applied in pulses that may last between 0.1 s to 30 s, 20 s, and/or 10 s. The most preferred embodiment produces plasma by voltage between electrodes in range between 100 V to 30 kV in more preferred embodiment between 1 kV to 30 kV in the most preferred embodiment in range between 1 kV to 20 kV. Plasma generation may use an electrode frequency of 20 kHz to 27 MHz in more preferred embodiment between 0.8 MHz to 15 MHz or in the most preferred embodiment between 1 MHz to 14 MHz.

Energy may be a thermal and/or cooling energy represented by an application of the heated and/or cooled fluid to the tissue. Fluid may be applied directly on the tissue.

The application of the first type of energy may also overlap with the application of second type of energy. The overlap of the first type of energy with the second type of energy may occur at discrete time intervals in the range of 0.01 to 100 seconds, more preferably in the range of 0.05 to 80 seconds, most preferably in the range of 0.1 to 60 seconds. The application of electromagnetic energy may be concurrently applied with the mechanical energy e.g. ultrasound energy transferred through the surface of same energy delivery element e.g. capacitive electrode.

The energy transfer may increase the temperature of the tissue in the range of 30° C. to 105° C., more preferably in the range of 32° C. to 70° C., even more preferably in the range of 34° C. to 55° C., most preferably in the range of 35° C. to 44.5° C. Optionally, the temperature of the tissue may be increased in the range 40.5° C. to 43.5° C.

The tissue may be cooled by a cooling and heating system. One or more layers and/or volumes of the tissue may be cooled. The one or more layers may be cooled, while the other layers may be heated. Optionally, tissue in one tissue layer may be heated while the non-treated tissue in the same tissue layer may be cooled by the device. Temperature of the tissue may be reduced in the range of −25° C. and 37° C., more preferably in the range of −15° C. and 30° C., even more preferably in the range of −10° C. and 28° C., most preferably in the range of −2° C. and 25° C. The tissue may also be cooled in order to maintain the normal body temperature on the surface while heating the inner layer or layers.

Treatment may include a treatment cycle of heating and cooling. The time interval of a cycle may be in the range of 0.05 to 1200 seconds, more preferably in the range of 0.01 to 1000 seconds, most preferably in the range of 0.5 to 800 seconds. The heating part of the treatment cycle of heating and cooling is preferably in the range of 0.1% to 90% of the cycle, more preferably in the range of 10% to 80% of the cycle, most preferably in the range of 35% to 70% of the cycle.

The method and device may use any type of energy mentioned in the Glossary. In addition, the method and device may use energy combination. The energy combination may be a combination of electromagnetic energy, electric energy, mechanical energy, thermal energy, magnetic energy and plasma with each other. A combination of electromagnetic energy and mechanical energy or plasma may be used. A combination of electromagnetic energy and magnetic energy or electric energy may be used. In another embodiment a combination of electromagnetic energy and thermal energy may be used, wherein the applied fluid may be heated by electromagnetic energy. Optionally, more types of electromagnetic energy may be used. Light may be combined with radiofrequency energy or microwave energy or radiofrequency energy may be combined with microwave energy. Optionally, types of mechanical energy, namely shock waves and ultrasound may also be combined.

Application of energy combinations may lead to higher comfort of the patient. By combining of first energy and second energy, the total output needed to provide a therapeutic effect may be the sum of the output of first and second type of energy. Therefore the output of one type of energy may be lower, because the combination with at least one other type of energy may provide sufficient therapeutic effect. Decreased output of one type of energy may reduce the possibility of burning, itching and/or pain.

Output of the first energy may participate in the total output pf the energy combination by portion of 50%, more preferably by portion of 55%, most preferably by portion of 65%.

One or more applicators may be used. The applicator may be positioned adjacent to the tissue and transfer energy into the tissue causing a biological effect. The applicator may include one or more detachable parts wherein the detachable part may be exchanged by the user in order to vary the treatment. The applicator may have one or more detachable part.

The physical appearance of the applicator (e.g. shape, size, length, width and/or elasticity) may be changed by adding and/or exchanging one or more detachable parts. Different and exchangeable detachable parts may provide operator choices of any physical appearance in order to sufficiently treat the tissue. The applicator may be assembled with a chosen length. Different parts of the applicator may have various widths to conform to anatomy of the body canals (e.g. vagina). Optionally, the utilization of one or more detachable parts may provide the applicator with none, one or more energy delivery elements located based on the operator's need. Such methods and devices may provide the applicator with adaptive detachable parts resolving problems of ineffective and uncomfortable treatment.

Detachable parts may include one or more energy delivery element for delivering energy to tissue. Optionally the detachable parts may not include any energy delivery element and be used e.g. for elongation of the applicator. Detachable parts may have various shapes, e.g. spherical, hemispherical, pyramidal, cuboid, prismatic, conical, annular and cylindrical. Prisms may have the base created by at least three, four or five lines creating triangular, tetragonal or pentagonal prism.

One or more detachable parts may be joined to one or more attaching elements which may contain a handle. A detachable part may be joined to another detachable part or attaching element containing the handle by e.g. a revolving mechanism.

One detachable part may be exchanged for another detachable part. In one exemplary embodiment a detachable part containing one energy delivery element may be replaced by different detachable part containing another one or more energy delivery element providing the same type or a different type of energy. A detachable part containing single energy delivery element may be replaced by different detachable part containing at least two energy delivery elements. In still another embodiment a detachable part containing single delivery element may be replaced by different detachable parts containing at least one or two energy delivery elements, where at least one energy delivery element located of the first detachable part may deliver same type of energy as the energy delivery element located of the second detachable part.

An applicator and/or one or more of its detachable parts may provide a sum of energy flux of the first energy and the second energy in the range between 0.0001 $W \cdot cm^{-2}$ to 2500 $W \cdot cm^{-2}$, more preferably in the range between 0.005 $W \cdot cm^{-2}$ to 1500 $W \cdot cm^{-2}$, most preferably in the range between 0.05 $W \cdot cm^{-2}$ to 1000 $W \cdot cm^{-2}$.

Any type of substance may be used before, after and/or during treatment. The substance may change the characteristics of the tissue e.g. provide analgesic effect, absorb applied energy, cause another biological effect to the treated tissue and/or target non-treated tissue in order to prevent the unintended biological effect in the treated tissue.

Optionally a fluid may be applied on the device and/or tissue to provide comfortable treatment and/or sufficient contact of the device and tissue. The fluid may be a hydrophobic or hydrophilic material having properties of a gel. Fluid may be applied from a reservoir.

The device of FIG. 1A may contain a power supply 101, which may include an emergency stop button 102. Power supply 101 may be connected to the central control unit 103, which may control one or more applicators 105. Central control unit 103 may contain and/or be connected to user interface 104. Connection of the central control unit 103 to the user interface 104 may be by wire and/or wireless. Power supply 101 may be part of the applicator 105 in the form of a disposable or rechargeable battery or power plug or standard power cord. Central control unit 103 may be also positioned in the applicator 105 or outside the applicator 105. Central control unit 103 may provide additional treatment control such as stabilization of the treatment parameters, for example frequency, power, impedance or temperature of treated tissue. Additional treatment control may be independent on the operator and may be provided because of safety of the treatment. Central control unit 103 may be coupled and/or communicate with storage tank 111, cooling and heating system 110, energy delivery element 108, power supply 101, energy generator 106 and/or sensor 112.

User interface 104 may be e.g. notebook, PC, mobile phone, tablet and/or control panel including a display, buttons and/or other control members. User interface 104 may contain one or more movement control devices for controlling the movement of the applicator. Such movement control device may include for example a joystick, keyboard, mouse, sleeve and/or electronic glove with the moves virtually transferred to the movement of the applicator and/or device. The applicator may be moved by robotic apparatus controlled by the operator. A movement control panel may be used to move the applicator without the need for the operator to contact intimate parts of the patient. This may reduce discomfort of the patients. A display may be part of the user interface providing set-up of the treatment, providing results of imaging and/or sensing the conditions and/or changes of the conditions of the tissue. Optionally, the display may also visualize the information about the treatment, such as length of the treatment, amount of transferred energy, data from sensors etc. Optionally, the user interface 104 may be part of the applicator 105.

The device may contain an energy generator 106 positioned inside or outside of the applicator 105. The energy generator may generate and/or regulate one or more types of energy for treatment. The device may include more than one energy generator (e.g. in case of more than one type of energy delivered to the body). The energy generator 106 may, if used may include a high frequency (HF) generator and transmatch adjusting the input impedance to the impedance of the treated tissue in order to maximize the power transfer. The energy generator 106 may also contain balun transformer.

The device may be in direct contact (shown in FIG. 1A), indirect contact (shown in FIG. 1B) or in no contact with the tissue 109.

In the case of direct contact, shown in FIG. 1A, the device (e.g. casing 107 or energy delivery element 108) may contact the tissue 109. Treated tissue may be tissue layer and/or tissue layers in direct contact and/or may be located below the contacted layer or layers of the tissue.

Figure 1B:
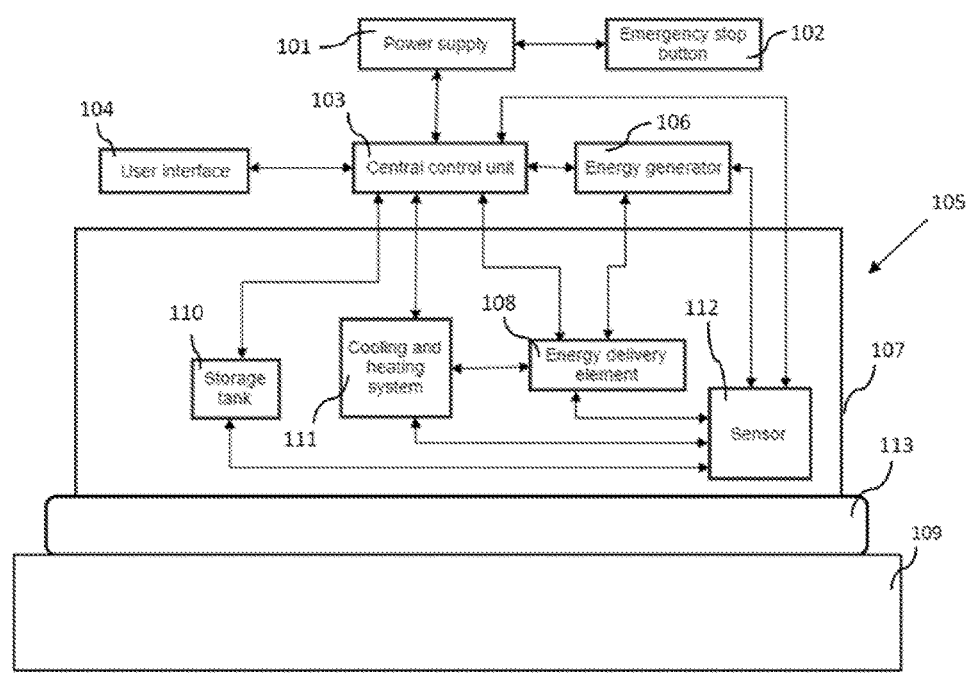
FIG. 1B is another schematic diagram of a device for treatment of tissue.

In case of indirect contact, shown in FIG. 1B, the gap between the tissue and the applicator may be filled by one or more spacing objects 113 (e.g. foam, bolus filled with fluid, waveguide, solid insulator, textile, solid mask and/or solid mask with holes). The spacing object 113 may cover at least part of surface of the applicator 105 and may be moved before, during and after the treatment by an automated system and/or manually. The spacing object may be profiled i.e. be thinner below the center of the energy delivery element than on the edge of the energy delivery element. The thickness of profiled spacing object below the center of the energy delivery element may at least 0.1 mm or 0.5 mm or 1 mm or 2 mm and up to 20 mm. Optionally, the thickness of the spacing object below the edge of energy delivery element may be at least 5% or 10% or 20% or 50% or 100% or 300% thicker than below the center of the energy delivery elements. The spacing object 113 may be detachable from the applicator 105. One or more spacing objects 113 may be positioned on the tissue separately from the applicator 105 prior the treatment. In another configuration, a plurality of spacing objects may be positioned on different parts of the surface of the tissue and the applicator is mounted to every one of them during the treatment. Spacing objects may be disposable or reusable e.g. after sterilization by autoclaving, gamma ray radiation, X-ray radiation and/or chemical sterilization.

In case of no contact with the tissue, the applicator may be spaced from the tissue by an gap filled e.g. by air. Preferred embodiments of this configuration are described below. The direct, indirect and/or method of the treatment with no contact may be changed during the treatment.

The device may contain functional parts e.g. a cooling and heating system 110, storage tank 111, energy delivery element 108 and sensor 112. These functional parts may be connected to the central control unit 103. Optionally, these parts may be located outside the applicator 105.

The device may contain a cooling and/or heating system 110. The cooling may be used for maintaining an increase or decrease in temperature of the device, applicator, energy delivery element and/or tissue. In first embodiment temperature-transferring media may be used. The media may be fluid (e.g. liquid or gas, preferably air) or a solid temperature-transferring part. Fluid may flow near and/or in contact with the energy delivery element 108 or any other part of device. The solid temperature-transferring part may be a thermoelectric device in contact with an electrode and/or the tissue. The flow of fluid may be provided by a blower or suction mechanism. The thermoelectric device may be also used for cooling the flowing fluid, which may then cool the device. In another embodiment the cooling and heating may be provided by a capacitive electrode located inside the device.

The cooling and/or heating system 110 may induce gentle heating. The heating generated by energy delivery element may not provide biological effect. Such change of temperature may be utilized to better match the temperature of the patient's tissue with the device, preventing temperature shock and constriction of the tissue touched by the device, applicator and/or energy delivery element. The cooling and heating system 110 may provide heating used for treatment of the tissue. Such configuration may be used with an energy delivery element 108 providing almost no heating (e.g. magnetic coil). The tissue may be preheated and/or pre-cooled before the start of the therapy The spacing object 113 may be also used for providing cooling and/or heating. Temperature-transferring media may be located in the spacing object and/or in the space between the spacing object and the energy delivery element.

The device may contain one or more storage tanks 111 for storing of one or more substances e.g liquid, gel or gas.

A substance, which may be a liquid, gel and/or gas, may be dispensed on the tissue and/or the part of the applicator. The substance may be dispensed before, during or after treatment. The substance (e.g. hydrating gel or water) may lower friction between the applicator and the tissue or improve conductivity for better energy transfer. In use of another, substance (e.g. antibiotics) may disinfect the surface of the tissue and/or the applicator. A substance (e.g. lidocaine) may provide an analgesic effect. The substance may also be a mixture of pharmaceutical products. The substance may be a single gas or a mixture of gases. Nitric oxide may be used to vasodilation of blood vessels or enhancement of sexual arousal. A gas and/or mixture of gases may be used to create a nonthermal plasma to help with healing of an irritated tissue from application of a capacitive, resistive electrode and/or one or more protruding invasive members (e.g. needles acting as electrodes).

The device may include one or more sensors 112 used for detecting changes or state of the treatment, input energy, transferred energy, reflected energy, tissue, applicator, energy delivery element and/or device, The sensor 112 may be an acoustic, vibration, chemical, electric, magnetic, radio, flow, navigation, positional, optical, imaging, pressure, force, density, temperature, impedance, current, Hall and/or proximity sensor. The sensor may be also gyroscope, capacitive displacement sensor, thermographic camera, ion selective electrode, pH electrode, and a like.

Measured physical quantities may be energy, impedance, temperature of one or more layers of the tissue, energy delivery element and/or the device, water content of the tissue, phase angle of delivered and/or reflected energy, pH of the environment, density of the tissue and the like.

The imaging sensor may be used for imaging of the region. The imaging sensor may be e.g. one or more cameras, an ultrasound transducer and/or terahertz imaging element. The imaging sensor may be a thermographic camera measuring the temperature of the treated and/or untreated tissue. The temperature sensitivity of the infrared camera may be better than 0.1 K or 0.5 K. The imaging sensor may provide a static picture and/or recorded footage of any abnormality inside the canal and/or cavity, on the visible surface of the tissue and/or in one or more layers of the tissue. The imaging device may be used to control the movement of the applicator by the operator from another room.

One sensor may also measure more than one physical quantity.

The sensor may be also a nerve detector. Such sensor may provide information about a presence of a nerve. For example, the sensor may provide low current to the tissue in order to stimulate the nerves. The response of the tissue may be monitored in order to approximately locate the innervated area.

The sensor may also sense a contact of the applicator with the tissue and/or a distance between the applicator and the tissue. Such sensor may be capacitive and/or impedance sensor. The system and method may be adapted to receive such signal in order to control the contact. Data from such sensor may be used to notify the operator about sufficient and/or unintended contact of the tissue and the device.

Data from one or more sensors may provide feedback of the device. Feedback may include a change of recommended time of treatment, automatic movement of the applicator, change of energy characteristics (e.g. frequency and/or power), change of position of the applicator based on patient's movement and the like. The feedback may include a determination of contact between the applicator and the tissue from the measurement of impedance.

The method and device may include usage of one or more sensors providing guidance to the applicator. A main problem during the treatment is linear movement of the applicator regardless the inner anatomical structure. Improper movement may cause unpleasant or painful treatment and may even lead to damage of the tissue. Use of such sensors may eliminate these treatment problems. The applicator may include one or more sensors, for example a sensor using electromagnetic and/or sound waves.

Data from the sensor may provide information about changes related to treatment. If a treatment characteristic exceeds a safety limit, the method and device may generate a signal in human perceptible form, e.g. sound or a color change. More than one signal may be generated. Alternatively, or additionally, and the method and device may immediately or gradually interrupt the treatment. Exceeding a safety limit may be signalled by flashing color LED located in the applicator and/or in the user interface together with a warning sound.

The method and device may include using of one or more applicators 105 containing one or more detachable parts. The device, particularly the applicator, may include one or more energy delivery elements delivering energy to the tissue.

The applicator 105 may be an internal applicator for internal use and/or external applicator for external use. The device may be used with one and/or both applicators. The device may provide treatment of external and internal parts of the tissue using the single applicator resembling a combination of both internal and external applicator. Applicators may be disposable and used for a single treatment or reusable and sterilized after every treatment and reused for another treatment.

The applicator may be made of polymer, metal, textile and/or any other biocompatible material. The materials may be varied, so the whole applicator may be made from variety of the materials. The surface of the applicator may be covered by one or more materials different from the surface material, for example by textile and/or membrane.

The applicator may include at least one focusing element for focusing energy to the point, area and/or layer of the tissue. The focused area may also include one or more layers of the tissue.

The one or more energy delivery elements may be a unipolar, monopolar, bipolar or multipolar electrode; coil; light source (e.g. LED diode, discharge tube, gas-discharge lamp, etc.); mechanical wave transmission element (e.g. piezo element); heating and/or cooling element and/or plasma delivery element.

One or more energy delivery elements may provide energy continuously or discretely e.g. in pulses. Energy delivery elements may be supported by another type of energy. Optionally, one or more energy delivery elements may provide energy discretely, and one or more another energy delivery elements may provide energy continuously.

Energy delivery elements may be provided in various shapes, sizes and orientations. The energy delivery element or elements may create a matrix, where the one or more energy delivery elements may have various shapes e.g. rectangular, circular, oval, annular or helical on the surface and/or around the applicator. Also, one or more energy delivery elements may cover the surface of the detachable part in the range of 2% to 100%, more preferably in the range of 5% to 100%, most preferably in the range of 12% to 100% of the surface of the detachable part.

Figure 2:
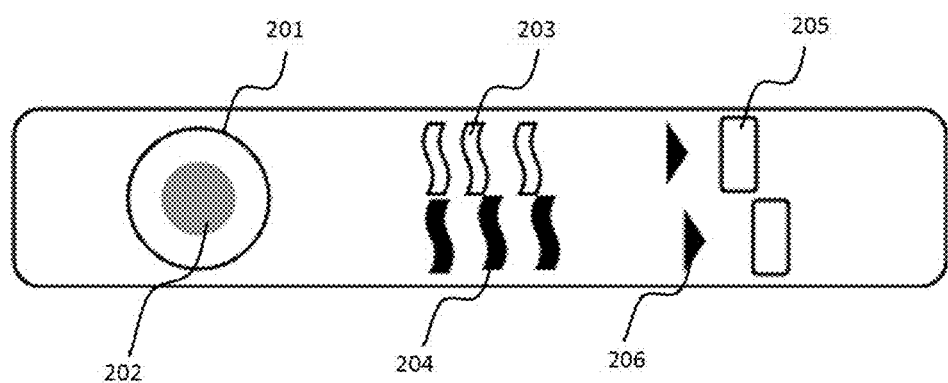
FIG. 2 is an exemplary embodiment of the energy delivery elements located of the applicator.

FIG. 2 illustrates energy delivery elements located on the applicator 105. A first energy element is depicted by a circle 201, while second energy delivery element is shown as a disc 202. In another embodiment energy delivery elements shown as the strips are located near to each other. Strips 203 and 204 may be energy delivery elements of the same or different type of the energy. In another embodiment embedded triangular elements 205 may be energy delivery elements delivering a first type of energy while and the healing delivery element 206 (e.g. plasma delivery element) may be located in a spatially different arrangement.

One or more energy delivery elements may be movable. The movement of one or more energy delivery elements may be circular, linear or in vertical direction in the relation to the treated tissue. These types of movements may be combined. Movement of one or more energy delivery elements may be used for providing a mechanical massage. The position of the one or more energy delivery elements may be adjusted according patient's needs and/or movement.

Treatment by one or more energy delivery elements may be controlled by central control unit 103. The central control unit 103 may provide treatment by one or more energy delivery elements. The central control unit 103 may provide treatment by all energy delivery elements.

One or more energy delivery elements and/or at least part of the energy delivery element may be detachable. An insulating layer of a capacitive electrode may be detachable to change the energy delivery element from a capacitive electrode to a resistive electrode.

The energy delivery element may invasively penetrate into the tissue via a penetrating member such as a needle.

An internal applicator may be positioned into and treat body canals and cavities e.g. the vagina, vulvar vestibule, cervix, urethra, rectum, anal canal, rectum, bladder, nose or mouth. An internal applicator may be also employed to treat external tissue. The labia minora, vulvar vestibule including labia minora and vaginal opening may be treated by an internal applicator.

The internal applicator may be of suitable shape e.g. a tubular and circular shape. The shape may include one or more ridges and/or incurvations providing a broader and/or thinner part.

Figure 3A:
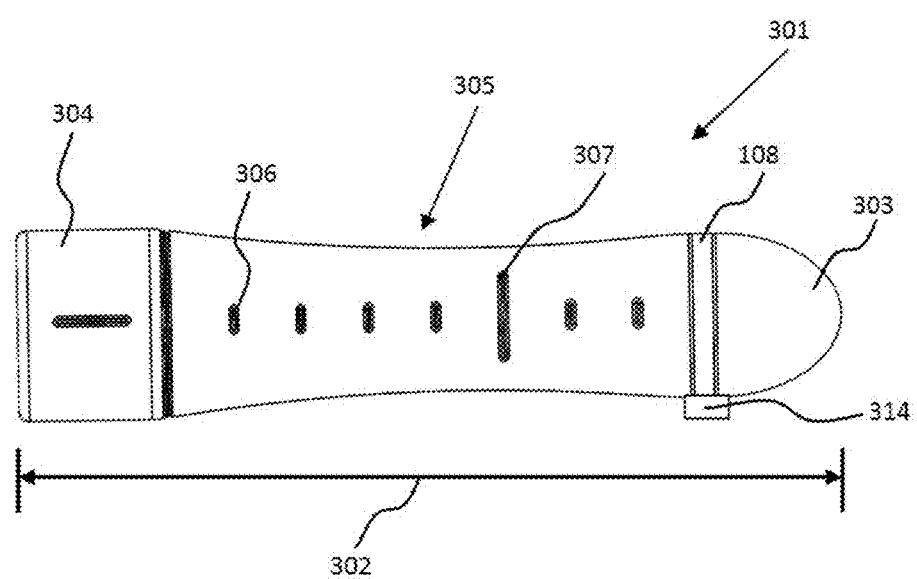
FIG. 3A is a view of an exemplary internal applicator.

FIG. 3A shows an internal applicator 301. The internal applicator 301 may have phallic shape. The length 302 of internally insertable part may be in the range of 0.5 cm to 25 cm, more preferably in the range of 0.75 cm to 20 cm, even more preferably in the range of 1 cm to 18 cm, most preferably in the range of 1.2 to 15 cm. The energy delivery element 108 (e.g. a monopolar capacitive electrode) is shown as a circular electrode around the distal part 303 of the applicator, although it may be also semicircular. It may be part of the distal part 303, curvature 305 and/or proximal part 304 of the internal applicator. The energy delivery element may have width in the range of 0.1 mm to 100 mm, more preferably in the range of 0.3 mm to 80 mm, even more preferably in the range of 0.5 mm to 60 mm, most preferably in the range of 1 mm to 50 mm. The radius of the circular and/or semicircular energy delivery element 108 may be in the range of 0.1 cm to 25 cm, more preferably in the range of 0.2 cm to 20 cm, even more preferably in the range of 0.4 cm to 15 cm, most preferably in the range of 0.5 cm to 12 cm.

The phallic shape of the internal applicator may be altered by the presence of one or more curvatures 305 having a radius of curvature in the range of 50 mm to 600 mm, more preferably in the range of 100 mm to 550 mm, even more preferably in the range of 120 mm to 500 mm, most preferably in the range of 135 mm to 450 mm.

A plurality of marks (e.g. smaller marks 306 and/or larger marks 307). may be equidistant to each other. Distance between the marks may be 0.1 cm or 0.2 cm or 0.25 cm or 0.5 cm or 1 cm or 1.5 cm and/or 2 cm. The marks may determine the length and/or volume of the applicator inserted into the body cavity and/or canal.

Figure 3B:
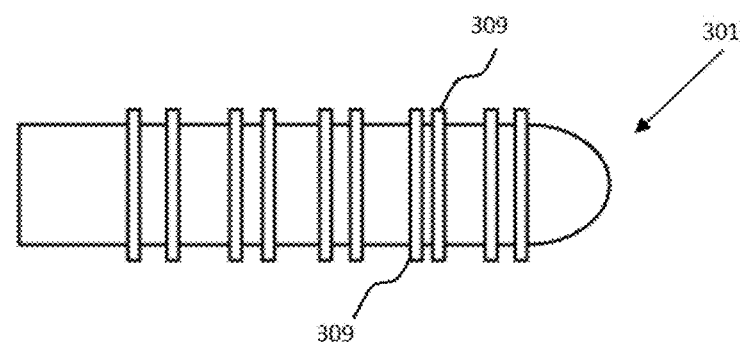
FIG. 3B is another view of an exemplary internal applicator.

FIG. 3B shows another embodiment, where the internal applicator 301 may carry one or more circular and/or semicircular energy delivery elements, e.g. bipolar electrodes 309, where complementary pairs of circular electrodes may be positioned close to each other. Optionally, the energy delivery element may be divided into segments, as shown on the FIGS. 4A-B. Distance between two energy delivery elements may be in the range of 0.01 mm to 20 mm, more preferably in the range of 0.05 mm to 15 mm, even more preferably in the range of 0.2 mm to 12 mm, most preferably in the range of 0.5 mm to 10 mm.

The energy delivery elements of the internal applicator may not touch the tissue at all. The one or more energy delivery elements can be located inside the curvature 305, which may be located in the free space formed by wider part of the applicator surrounding the ridge. The internal applicator may include a grid contacting the tissue and spacing the tissue from the energy delivery element.

Figure 3C:
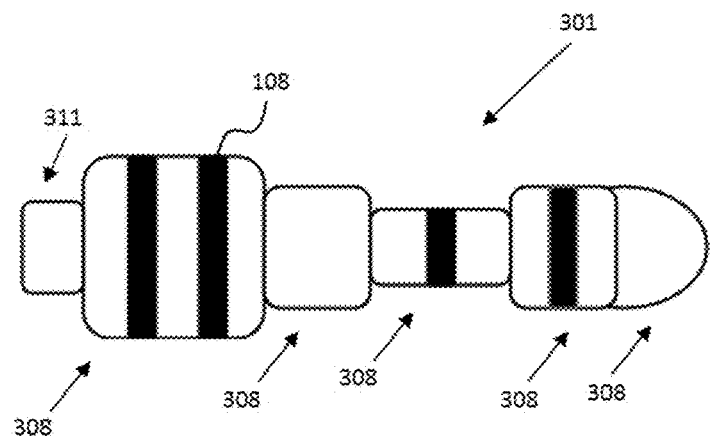
FIG. 3C is another view of an exemplary internal applicator.

FIG. 3C shows an embodiment of the internal applicator divided into several e.g. circular or semicircular detachable parts 308 attached to attaching part 311, some of them carrying their own energy delivery element 108. The detachable parts 308 have various lengths, shapes and/or widths. Therefore, they may be combined to create a differently sized and ridged applicator.

Figure 3D:
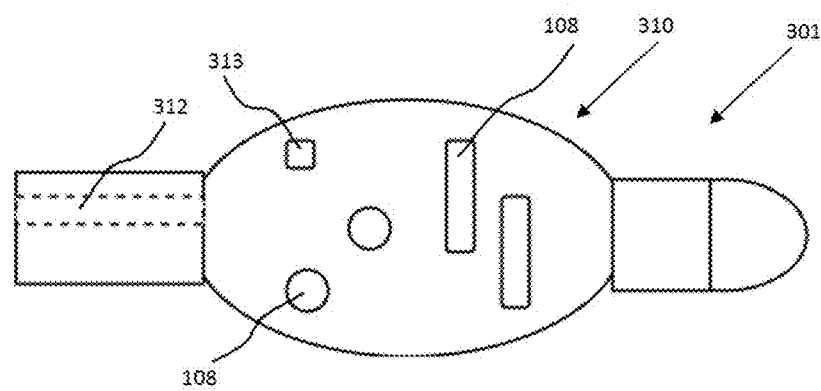
FIG. 3D is another view of an exemplary internal applicator.

In FIG. 3D the internal applicator 301 may include one or more expandable elements 310 made from elastic material, where one or more energy delivery elements 108 is located on the surface of the expandable element 310. FIG. 3D shows more energy delivery elements 108 with different shapes. One or more expandable elements 108 may also be detachable parts. During the treatment, the expandable element 310 may be filled with fluid. Filling fluid may be warm or cold and be stored outside the internal applicator 301 and/or inside the storage tank 111. In both cases, the fluid may be transferred to expandable element 310 by one or more nozzle 312. Then, the fluid may be drained from the expandable element 310 by the same nozzles.

The cold fluid may cool the tissue during application of the energy while the warm fluid may provide relaxation to the tissue and ensure the deeper insertion of the applicator. Presence of cold fluid and warm fluid may be alternated in time periods. By alternating cold-warm fluid, the first fluid may be present in the range of 5% to 100%, more preferably in the range of 10% to 100%, even more preferably in the range of 20% to 100% of total therapy time. The expandable element may be partially or totally filled at specific times during the treatment. Partial filling may be used for prevention of shock or injury of the tissue. The volumetric flow rate through one nozzle during the transfer of the fluid in and/or out the expandable element may be in the range of 0.001 $mm^3/s$ to 1 $dm^3/s$, more preferably in the range of 0.1 $mm^3/s$ to 0.5 $dm^3/s$, even more preferably in the range of 0.15 $mm^3/s$ to 0.25 $dm^3/s$, most preferably in the range of 0.2 $mm^3/s$ to 0.1 $dm^3/s$. The expandable element 310 may include a pressure sensor and/or a proximity sensor 313. A proximity sensor may be positioned on the surface of and/or in the expandable structure. The proximity sensor may be impedance sensor.

The internal applicator may also include one or more rotational apparatus, which may provide rotational movement to the applicator and/or its parts. The present methods and devices may use rotational movement to provide treatment to the whole surface of the cavity and/or canal without any manually challenging movement by the operator. This may lead to reduced movement of the applicator. One or more detachable parts 308 or the internal applicator 301 may be rotated around a longitudinal axis, or. the whole internal applicator may be rotated around its longitudinal axis. Optionally, one of complementary electrodes of the bipolar pair may be rotated.

FIG. 4A shows a circular energy delivery element 108 divided to segments 401a-401e. Energy delivery element 108 may be divided to at least two, three, four or more than four arcs similar to the segments 401a-401e. Angular sections of the segment 401 (e.g. 401a) may be in the range of 1° to 359° or 5° to 275° to 15° to 185° or 20° to 95°. Arcs 401a and 401b may transfer energy to upper part of tissue (e.g. vagina), while the other segments are deactivated. Other segments may be activated after the ceasing operation of segments 401a-b and/or during the operation of segments 401a-b. Segments 401a-e may be independently controlled in order to deliver the energy to close parts of the tissue. In FIG. 4B the energy delivery element 108 is divided into one or more layers. At least part of the energy delivery element may be divided into at least two layers as represented by layers 402a and 402b. Optionally, one or more segments 401a-e may be divided into layers 402a-b. Segments 401a-401e and layers 402a-b may be detachable from the applicator and act as a detachable element 308.

The internal applicator may include a shield member 314 protecting an urethral orifice and/or urethra. Such shield member may provide decreased occurrence of adverse events including e. g. urinary tract infection. It may be e.g. plastic cover on one side surface of the insertable part of the applicator. Optionally it may be a membrane plug and/or membrane surface covering the urethra during the treatment. It may also be an additional energy delivery element positioned closely to the urethral orifice devoted to apply such type and/or of energy to tighten the urethra during the treatment. As already mentioned, the energy delivery element may form the semicircular shape. The shield member may therefore be a complement to the semicircular energy delivery element. Thus, the shield member and energy delivery element may create joint circular shape resembling the circular energy delivery element shown on FIG. 2. In such case, the energy delivery element may form the at least 45%, more preferably 55%, even more preferably 65%, most preferably 80% of the joint circular shape.

The internal applicator 301 may also be distanced from the tissue by a spacing object. In such configuration, the thickness of the spacing object may be in the range of 0.01 cm to 2 cm, more preferably in the range of 0.03 cm to 1.5 cm, even more preferably in the range of 0.05 cm to 1.25 cm, most preferably in the range of 0.1 cm to 1 cm. The spacing object may be filled with fluid, e.g. water, silicone, ethylene glycol, polymer fibres, carbon dioxide and/or air.

Optionally, the applicator may be in a form of a thin structure e.g. a flexible structure containing an energy delivery element inserted into the tissue in the rolled form, where it may be unrolled.

The external applicator may be positioned above the tissue which may include female genital tissue and/or its surrounding external tissue. FIG. 5A illustrates the external applicator 501 not contacting the tissue 109. The applicator may be positioned by one or more mechanical arms 502 and/or by hand. Joints 503 may adjust shape and/or position of external applicator 501 by movement of one or more adjustable elements, e.g. outer adjustable element 504 and/or inner adjustable element 505. The external applicator may also include only one adjustable element. Adjustable elements and/or joints 503 may contain energy delivery elements, sensors. One and more adjustable elements and/or joints may be detachable.

One and more parts of the external applicator and/or mechanical arm may contain and/or be attached to a motor unit 506 providing movement. Optionally, one or more portions of the device may be moved manually. The applicator may be moveable in one or more axis of Cartesian coordinate system. Movement may be represented by rotation, tilting and/or translation movement of portions of the device. The movement may provide sufficient adaptation of the applicator to the anatomy of the human body. Inner adjustable elements 505 and/or outer adjustable elements 504 may be tilted to be positioned adjacent to the treated tissue.

The position of the device and/or its parts may be tracked by a sensor 507 for obtaining feedback. The sensor may be an inclinometer, an accelerometer, a load cell, a force sensor, a magnetic sensor, a distance sensor and/or an optic sensor.

The external applicator and/or one or more its parts may be positioned in a static position or it may be moved during treatment. Portions of the device may be moved and repeatedly stopped in predetermined positions during treatment. The static position in the predetermined position may be provided by a locking mechanism 508. The locking mechanism may be mechanical e.g. latching member, screw mechanism, self-locking mechanism such as worm gearing, electromagnetic and/or magnetic e.g. electromagnetic brake.

The external applicator 501 may be distanced from the tissue by a gap. The gap may be an air gap, or a fluid gap which may change the characteristic of the transferred energy, e.g. it may provide inhibition of electric energy and/or magnetic energy of electromagnetic radiation. Adjustable parts and/or joints may include nozzles and/or other known technical solutions speeding air circulation through the gap in the vicinity of the tissue. Air circulation may provide cooling effects together with control of perspiration. Other kinds of fluid e.g. water vapour, inert gases (e.g. noble gases, nitrogen) and carbon dioxide may also be used. The thickness of the gap may be in the range of 0.01 cm to 50 cm, more preferably in the range of 0.03 cm to 35 cm, even more preferably in the range of 0.05 cm to 30 cm, most preferably in the range of 0.1 cm to 25 cm. Thickness of the gap may be constant or variable during the treatment.

The external applicator 501 may also be distanced from the tissue by a spacing object. In such configuration, the thickness of the spacing object may be in the range of 0.01 cm to 50 cm, more preferably in the range of 0.03 cm to 35 cm, even more preferably in the range of 0.05 cm to 30 cm, most preferably in the range of 0.1 cm to 25 cm. The spacing object may be filled with fluid, e.g. water, silicone, polymer fibres and/or fluids mentioned above.

Figure 5B:
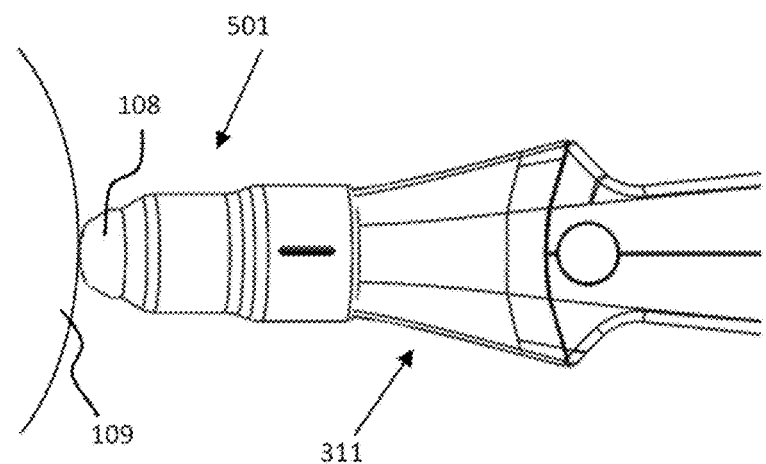
FIG. 5B is another view of an exemplary external applicator.

FIG. 5B shows an external applicator 501 attached to a part of a device through an attaching part 311. Energy delivery element 108 is shown in contact with tissue 109. The conical-shape of the external applicator shown in FIG. 5B may provide smooth and soft treatment. The length of the energy delivery element of the applicator may be in the range of 0.01 cm to 25 cm, more preferably 0.05 cm to 20 cm, even more preferably 0.1 cm to 17 cm, most preferably 0.2 cm to 15 cm.

The external applicator may also have shape of an undergarment, sanitary napkin, panties, C-string, diaper and/or trousers, with the external applicator worn during common activities.

The external applicator may treat a patient without the necessity of removing the underwear and/or clothes. All types of applicators may be incorporated into support structures (e.g. bed or chair).

The methods of treatment are performed by the operator i.e. the patient or a medical professional such as a doctor, nurse or technician. Such treatment may be done at home, at beauty salon and/or in a hospital. Generally, a medical professional is not needed and the treatment may be characterized by executing the method and applying the energy under the control of the patient e.g. by strictly manual movement of the applicator.

The methods and devices may be self-operated. Self-operated treatment may be characterized by the initial manual configuration of the device followed by automated and/or corrected treatment of the tissue. Optionally, self-operated treatment may be performed without initial manual configuration. In this case, the system may set all the parameters according to its calibration.

The method and device may include automatic feedback based on information from one and more sensors measuring e.g. temperature, impedance, phase angle of reflected energy, phase angle of delivered energy and/or pressure. The feedback may include the slowing and/or ceasing of penetration of the device into the cavities and/or canals (e.g. vulvar vestibule and/or vagina), change of pressure in the expandable element, change of energy characteristics (frequency, power output), change of treatment time and temperature of the device. Additionally, feedback may include activation and/or deactivation of at least one energy delivery element delivering different type of energy (e.g. plasma, mechanical energy).

The initial configuration may include the setting of the initial position of the applicator, one or more portion of the applicator, type of energy, one or more characteristics of the energy, type of first and second energy, desired temperature of the tissue, volume of fluid in the spacing object, volume of fluid in the expendable element, pressure in the spacing object, pressure in the expendable element, position of at least one energy delivery element, rotational velocity of the applicator, velocity of translational movement of the applicator and/or one or more its portions. Following treatment may include the change of all characteristics which are mentioned in relation to the initial configuration.

Concerning the initial location, the device and method including the internal applicator may be inserted into a cavity and/or canal, e.g. vulvar vestibule and/or vagina. The applicator may be positioned just in the vaginal opening, in the approximate centre of the vaginal canal, on the vaginal cervix and/or any other place between these locations. After the initial configuration the applicator may be left in the desired position or it may be continually or intermittently moved in an automatic mode from one position to another providing energy to the tissue. The initial location of the device including the applicator may alternatively be positioned adjacent to the tissue. The applicator may be in the direct contact with the tissue. After the initial configuration the external applicator and/or at least one of its portions may be inclined and/or inclined during the treatment, and the external applicator may move adjacent to the tissue.

The applicator may be initially configured to apply electromagnetic energy (e.g. light, radiofrequency energy and/or microwave energy). During the treatment, the application of electromagnetic energy (including light, radiofrequency energy and microwave energy) may be replaced with the application of mechanical energy (including ultrasound energy and shock wave energy), electric energy, thermal energy, magnetic energy and/or plasma. Treatment may require different energy type, depth, power focus. The frequency and/or power may be changed during treatment. Some of the energy replacement may also lead to a change of depth of treatment and/or focusing of the energy. The application of the mechanical energy (e.g. ultrasound and/or shock wave energy) may lead to creation of focus at a desired depth of the tissue and/or defocusing the energy into a larger area of the tissue. However, any other kind of energy may be provided in focused, nonfocused or a defocused manner.

The internal applicator may be initially inserted into a canal e.g. vagina, and then perform automated rotational and/or linear movement to treat the tissue.

One and more characteristics (e.g. temperature of the tissue, temperature of the energy delivery element, pressure etc.) of the treatment may be checked by at least one sensor before, during and/or after treatment and processed by the device. Processed information demanding awareness (e.g. loss of contact of the applicator with the tissue) may be signalled by any human perceptible signal (e.g. continuous and/or pulsing coloured LEDs, sound signal and/or vibration).

Optionally, the at least one characteristic and/or parameter may be corrected by the device. The parameter measured by sensor may be impedance, phase angle, contact, temperature, flux density and the like.

The sensor and/or operator may determine the friction and/or humidity of the tissue. In this case, the device may provide a human perceptible signal to inform the operator about the necessity of supplying the fluid and/or induce the reservoir to release an amount of fluid.

All parameters and characteristics of the treatment with respect to self-operated treatment may be corrected by the patient and/or operator.

The method and device may provide controlled local treatment of the tissue. The device may provide information about the tissue to be treated. For example, the anal canal, vaginal canal and/or external part of the genitalia may be divided into sectors, where the sectors to be treated may be identified by a sensor. The treatment may then aim at least one of this sectors according to its severity e.g. laxity.

The energy generator and/or energy delivery element providing RF energy may include or cooperate with a transmatch and/or a balancing/unbalancing element (e.g. balun), wherein at least one of the transmatch and/or balancing/unbalancing element is regulated by a control unit or e.g. by an SWR meter in order to tune power, phase, impedance and or amplitude of the RF energy.

The foregoing description of preferred embodiments has been presented for purposes of illustration and description. It is not intended to be exhaustive or to limit the invention to the precise form disclosed. Modification and variations are possible in light of the above teachings or may be acquired from practice of the invention. All mentioned embodiments may be combined. The embodiments described explain the principles of the invention and its practical application to enable one skilled in the art to utilize the invention. Various so modifications as are suited to a particular use are contemplated. It is intended that the scope of the invention be defined by the claims appended hereto and their equivalents.

The invention claimed is:

1. A method for a genital tissue treatment comprising:
    making an assembled applicator by attaching at least one detachable part to an applicator;
    wherein the at least one detachable part includes at least one circular energy delivery element encircling or around the detachable part;
    with the at least one circular energy delivery element having a width in a range of 0.1 mm to 100 mm and a radius in a range of 0.5 cm to 12 cm and covering 2% to 100% of the surface of the detachable part;
    positioning the assembled applicator having a length in a range of 0.75 cm to 20 cm into or onto genital tissue;
    transferring radiofrequency energy into the genital tissue;
    wherein the radiofrequency energy is in a range of 350 kHz to 100 MHz with an output up to 450 W providing energy flux in a range of 0.001 W·cm−2 to 1500 W·cm−2; and
    heating genital epithelium.

2. The method of claim 1 wherein the at least one detachable part further includes an energy delivery element delivering mechanical wave energy.

3. The method of claim 2 wherein the energy delivery element delivering mechanical wave energy provides ultrasound energy having an energy flux in the range of 0.001 W·cm−2 to 500 W·cm−2.

4. The method of claim 1 wherein the at least one detachable part is expandable.

5. The method of claim 1 wherein the applicator includes at least one impedance sensor in communication with a central control or an energy generator and providing feedback during treatment, wherein the feedback provides a human perceptible signal or deactivates the at least one energy delivery element.

6. The method of claim 1 wherein the applicator includes at least one impedance sensor in communication with a central control or an energy generator and providing feedback during treatment, wherein the feedback includes changing an output power or a temperature of the at least one energy delivery element.

7. The method of claim 1 wherein the applicator includes at least one temperature sensor in communication with a central control or an energy generator and providing feedback during treatment, wherein the feedback includes changing an output power or a temperature of the at least one energy delivery element.

8. The method of claim 1 wherein the heating of the genital epithelium is used for pain relief.

9. A method for a vaginal tissue treatment comprising:
    making an assembled applicator by attaching at least one detachable part to an applicator;
    with the applicator including at least one circular energy delivery element encircling or around the applicator;
    with the at least one circular energy delivery element having a width in a range of 0.1 mm to 100 mm and a radius in a range of 0.5 cm to 12 cm;
    positioning the assembled applicator having a length in a range of 0.75 cm to 20 cm into or onto vaginal tissue;
    transferring radiofrequency energy into the vaginal tissue;
    wherein the radiofrequency energy is in a range of 350 kHz to 100 MHz with an output up to 450 W providing energy flux in a range of 0.001 W·cm−2 to 1500 W·cm−2; and
    heating vaginal epithelium tissue.

10. The method of claim 9 wherein the vaginal epithelium tissue is heated in a range of 34° C. to 55° C.

11. The method of claim 10 wherein the applicator includes at least one impedance sensor in communication with a central control or an energy generator and providing feedback during treatment, wherein the feedback includes activation or deactivation of the at least one energy delivery element.

12. The method of claim 11 wherein the applicator includes at least one temperature sensor in communication with the central control or the energy generator and providing the feedback during treatment, wherein the feedback includes changing output power or temperature of the at least one energy delivery element.

13. The method of claim 12 with the at least one energy delivery element covers 2% to 100% of a surface of the applicator.

14. The method of claim 13 wherein the applicator includes the at least one impedance sensor in communication with the central control or the energy generator and providing the feedback during treatment, wherein the feedback includes changing output power or temperature of the at least one energy delivery element.

15. The method of claim 14 wherein the heating of the vaginal tissue is used for blood flow enhancement.

16. The method of claim 15 wherein the applicator with the at least one detachable part further provides ultrasound energy having an energy flux in the range of 0.001 W·cm−2 to 500 W·cm−2 and providing the ultrasound energy to the vaginal tissue.

17. A method for a pelvic floor tissue treatment comprising:
    making an assembled applicator by attaching at least one detachable part to an applicator;
    with the assembled applicator including at least two energy delivery elements providing a first type of energy;
    at least one of the energy delivery elements having a width in a range of 0.1 mm to 100 mm, with a distance between the at least two energy delivery elements in a range of 0.01 mm to 20 mm;

positioning the assembled applicator into or onto pelvic floor tissue;

transferring an energy into the pelvic floor tissue;

with a sum of energy flux from the energy delivery elements of the assembled applicator in a range of 0.0001 W·cm−2 to 2500 W·cm−2; and causing a biological effect in the pelvic floor tissue.

18. The method of claim 17 with the assembled applicator having a length in a range of 0.75 cm to 20 cm.

19. The method of claim 18 wherein the applicator includes at least one sensor providing feedback during treatment, wherein the feedback includes a change of power output.

20. The method of claim 19 wherein the applicator includes at least one temperature sensor providing the feedback during treatment, wherein the feedback includes activation or deactivation of the at least one energy delivery element.

21. The method of claim 20 wherein the applicator includes at least one impedance sensor in communication with a central control or an energy generator and providing the feedback during treatment, wherein the feedback includes activation or deactivation of the at least one energy delivery element.

22. The method of claim 21 with the at least one energy delivery element covering 5% to 100% of the surface of the at least one detachable part.

23. The method of claim 22 where the first type of energy is radiofrequency energy, with one of the energy delivery elements providing a second type of energy;

wherein the second type of energy is mechanical wave energy, and application of the radiofrequency energy is simultaneously applied with application of the mechanical wave energy.

24. A method for a pelvic floor tissue treatment comprising:

making an assembled applicator by attaching at least one detachable part to an applicator;

with the assembled applicator including first and second energy delivery elements delivering a first type of energy and a second type of energy, respectively;

with at least one of the energy delivery elements comprising a circular energy delivery element having a width in the range of 0.1 mm to 100 mm and a radius in the range of 0.5 to 12 cm, and a distance between the first and second energy delivery elements in the range of 0.01 mm to 20 mm;

positioning the assembled applicator into or onto pelvic floor tissue;

transferring energy into the pelvic floor tissue;

with a sum of energy flux from the energy delivery elements of the assembled applicator in the range of 0.005 W·cm−2 to 1500 W·cm−2; and causing a biological effect in the pelvic floor tissue.

25. The method of claim 24 wherein the tissue is heated to a range of 34° C. to 55° C.

26. The method of claim 25 with the at least one energy delivery element covering 2% to 100% of the surface of the at least one detachable part.

27. The method of claim 26 wherein the applicator includes at least one impedance sensor in communication with a central control or an energy generator and providing feedback during treatment, wherein the feedback includes activation or deactivation of the at least one energy delivery element.

28. The method of claim 27 wherein the applicator includes at least one temperature sensor in communication with the central control or the energy generator and providing the feedback during treatment, wherein the feedback includes changing frequency, output power or temperature of the at least one energy delivery element.

29. The method of claim 25 wherein the at least one detachable part is expandable.

30. The method of claim 28 where the first type of energy is radiofrequency energy and the second type of energy is mechanical wave energy, wherein application of the radiofrequency energy is simultaneous with application of the mechanical wave energy.

\* \* \* \* \*